United States Patent
Granger et al.

(10) Patent No.: US 7,499,632 B2
(45) Date of Patent: Mar. 3, 2009

(54) DEVICE FOR DISTRIBUTING VOLATILE FLUIDS IN AIR

(75) Inventors: David A. Granger, Syracuse, IN (US); Andrew J. Felton, Fort Wayne, IN (US)

(73) Assignee: Momentum Industries, LLC, Fort Wayne, IN (US)

( * ) Notice: Subject to any disclaimer, the term of this patent is extended or adjusted under 35 U.S.C. 154(b) by 290 days.

(21) Appl. No.: 11/686,682

(22) Filed: Mar. 15, 2007

(65) Prior Publication Data

US 2007/0217771 A1 Sep. 20, 2007

Related U.S. Application Data

(60) Provisional application No. 60/783,126, filed on Mar. 16, 2006.

(51) Int. Cl.
*A01G 13/06* (2006.01)

(52) U.S. Cl. .................. 392/386; 392/395

(58) Field of Classification Search .......... None
See application file for complete search history.

(56) References Cited

U.S. PATENT DOCUMENTS

| | | | |
|---|---|---|---|
| 1,229,363 A | 6/1917 | West | |
| 2,556,910 A | 6/1951 | Feldman et al. | |
| 2,603,468 A | 7/1952 | Sutton | |
| 2,614,820 A | 10/1952 | Boydjieff | |
| 2,653,017 A | 9/1953 | Frost | |
| 2,802,695 A | 8/1957 | Johnson | |
| 2,828,953 A | 4/1958 | Hartmann | |
| 3,661,838 A | 5/1972 | Enomoto | |
| 3,864,080 A | 2/1975 | Valbona et al. | |
| 4,064,203 A | 12/1977 | Cox | |
| 4,165,835 A | 8/1979 | Dearling | |
| 4,166,087 A | 8/1979 | Cline et al. | |
| 4,173,604 A | 11/1979 | Dimacopoulos | |
| 4,228,124 A | 10/1980 | Kashihara et al. | |
| 4,294,778 A | 10/1981 | DeLuca | |
| 4,323,193 A | 4/1982 | Compton et al. | |
| 4,346,059 A | 8/1982 | Spector | |
| 4,370,300 A | 1/1983 | Mori et al. | |
| 4,377,399 A | 3/1983 | Bryson | |
| 4,658,985 A | 4/1987 | Madsen et al. | |
| 4,703,070 A | 10/1987 | Locko et al. | |
| 4,781,895 A | 11/1988 | Spector | |
| 4,849,181 A | 7/1989 | Kelley et al. | |
| 4,891,904 A | 1/1990 | Tabita | |
| 5,000,383 A | 3/1991 | van der Heijden | |
| 5,029,729 A | 7/1991 | Madsen et al. | |

(Continued)

*Primary Examiner*—Thor S Campbell
(74) *Attorney, Agent, or Firm*—Bakers & Daniels LLP (57) ABSTRACT

A distribution device for distributing volatile fluids in air. In an exemplary embodiment, the distribution device includes a wick formed of a solid material which is impregnated with a volatile fluid, such as a scented liquid, a disinfectant, a fungicide, an anti-allergenic substance, an insect repellant, or an insecticide, for example. In another embodiment, the device includes a substantially hollow, tubular shaped wick which includes a portion that is exposed to the surrounding environment and a portion that is in liquid communication with a liquid reservoir containing a volatile fluid. The wick is positioned in the liquid reservoir and in a close fitting engagement with an open end of the liquid reservoir. The hollow configuration of the wick provides a greater exposed surface area to enhance the evaporation of the liquid into the surrounding environment.

23 Claims, 6 Drawing Sheets

U.S. PATENT DOCUMENTS

| | | |
|---|---|---|
| 5,114,625 A | 5/1992 | Gibson |
| 5,115,975 A | 5/1992 | Shilling |
| 5,175,791 A | 12/1992 | Muderlak et al. |
| 5,431,885 A | 7/1995 | Zlotnik et al. |
| 5,547,721 A | 8/1996 | Kuo |
| 5,567,361 A | 10/1996 | Harper |
| 5,572,800 A | 11/1996 | West |
| 5,810,265 A * | 9/1998 | Cornelius et al. ........... 239/690 |
| 5,861,128 A | 1/1999 | Vick et al. |
| 6,106,786 A * | 8/2000 | Akahoshi .................... 422/124 |
| 6,270,720 B1 | 8/2001 | Mandish |
| 6,334,974 B1 | 1/2002 | Chen |
| 6,379,689 B1 | 4/2002 | Aguadisch et al. |
| 6,604,733 B2 | 8/2003 | Mulvaney et al. |
| 2002/0023968 A1* | 2/2002 | Pedrotti et al. ................ 239/60 |
| 2003/0175171 A1 | 9/2003 | Yamamoto et al. |
| 2004/0262420 A1 | 12/2004 | Hansen et al. |
| 2006/0022064 A1 | 2/2006 | Triplett et al. |

\* cited by examiner

FIG_5

FIG_5A

FIG_5B

FIG_6

DEVICE FOR DISTRIBUTING VOLATILE FLUIDS IN AIR

CROSS REFERENCE TO RELATED APPLICATIONS

This application claims the benefit under Title 35, U.S.C. § 119(e) of U.S. Provisional Patent Application Ser. No. 60/783,126, entitled DEVICE FOR DISTRIBUTING VOLATILE LIQUIDS IN AIR, filed on Mar. 16, 2006, the disclosure of which is hereby expressly incorporated herein by reference.

BACKGROUND

1. Field of the Disclosure

The present disclosure relates to a device for distributing volatile fluids in air, such as an air freshening or air cleaning device for distributing a scented liquid or a disinfectant into a surrounding environment, for example. More particularly, the present disclosure relates to improved wick structures and associated distribution mechanisms and housings for such devices.

2. Description of the Related Art

Conventional devices for distributing volatile fluids in air typically employ a solid, substantially cylindrically shaped wick which extends into contacting, liquid communication with a volatile liquid contained in a reservoir, such as a scented liquid, for example. The liquid is carried along the length of the wick via capillary action toward an end of the wick disposed opposite the reservoir. Volatilization, or evaporation, of the scented liquid from the end of the wick into the surrounding air distributes the fragrance of the scented liquid into the surrounding environment.

The distribution device may include a distribution mechanism to enhance distribution of the volatile fluid into the surrounding environment. One such distribution mechanism is a fan which provides a flow of air across the end of the wick in a direction transverse to the wick. Another such device is a heating element disposed proximate the wick which heats the space around the wick and/or the wick itself to aid in evaporating the scented liquid to enhance distribution of the volatile liquid into the surrounding environment.

What is needed is a device for distributing volatile fluids in air which is an improvement over the foregoing.

SUMMARY

The present disclosure provides a distribution device for distributing volatile fluids in air. In an exemplary embodiment, the distribution device includes a wick formed of a solid material which is impregnated with a volatile fluid, such as a scented liquid, a disinfectant, a fungicide, an anti-allergenic substance, an insect repellant, or an insecticide, for example. In another embodiment, the device includes a substantially hollow, tubular shaped wick which includes a portion that is exposed to the surrounding environment and a portion that is in liquid communication with a liquid reservoir containing a volatile fluid. The wick is positioned in the liquid reservoir and in a close fitting engagement with an open end of the liquid reservoir. The hollow configuration of the wick provides a greater exposed surface area to enhance the evaporation of the liquid into the surrounding environment.

The device may further include a distribution mechanism to enhance the evaporation and distribution of the evaporated liquid into the surrounding environment. In one embodiment, the distribution mechanism may be a fan disposed near the end of the wick opposite the surrounding environment, the fan providing a flow of air through a central passage defined by the hollow portion of the wick. Advantageously, forcing air through the central passage of the wick provides direct contact between the air flow and a greater surface area of the wick than in known devices which include wicks having solid cross-sections, in order to enhance the evaporation and distribution of the liquid from the wick into the surrounding environment. In another embodiment, the distribution mechanism may be a heating element disposed proximate, at least partially within, or entirely within, the central passage of the wick. The heating element heats the central passage of the wick and the wick itself to enhance volatilization and evaporation of the liquid, and also sets up a convection air flow through the central passage of the wick to further enhance distribution of the evaporated liquid into the surrounding environment.

In one form thereof, the present disclosure provides a device for distributing a fluid into a surrounding environment, including a housing; a solid wick defining a passage therethrough, the wick impregnated with a fluid, the wick in airflow communication with the housing and the surrounding environment; and an activating element positioned within the housing for effecting distribution of the fluid into the surrounding environment.

In another form thereof, the present disclosure provides a device for distributing a fluid into a surrounding environment, including a housing including a reservoir containing a fluid; the reservoir including an inner wall and an outer wall defining an opening; a substantially hollow wick defining a passage therethrough, the wick in fluid communication with the surrounding environment and the housing, the wick disposed between the inner wall and the outer wall, the wick abutting both the inner wall and the outer wall; and an activating element disposed at least partially within the housing for effecting distribution of the fluid into the surrounding environment.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure, and such exemplifications are not to be construed as limiting the scope of the invention in any manner.

DETAILED DESCRIPTION

Figure 1:
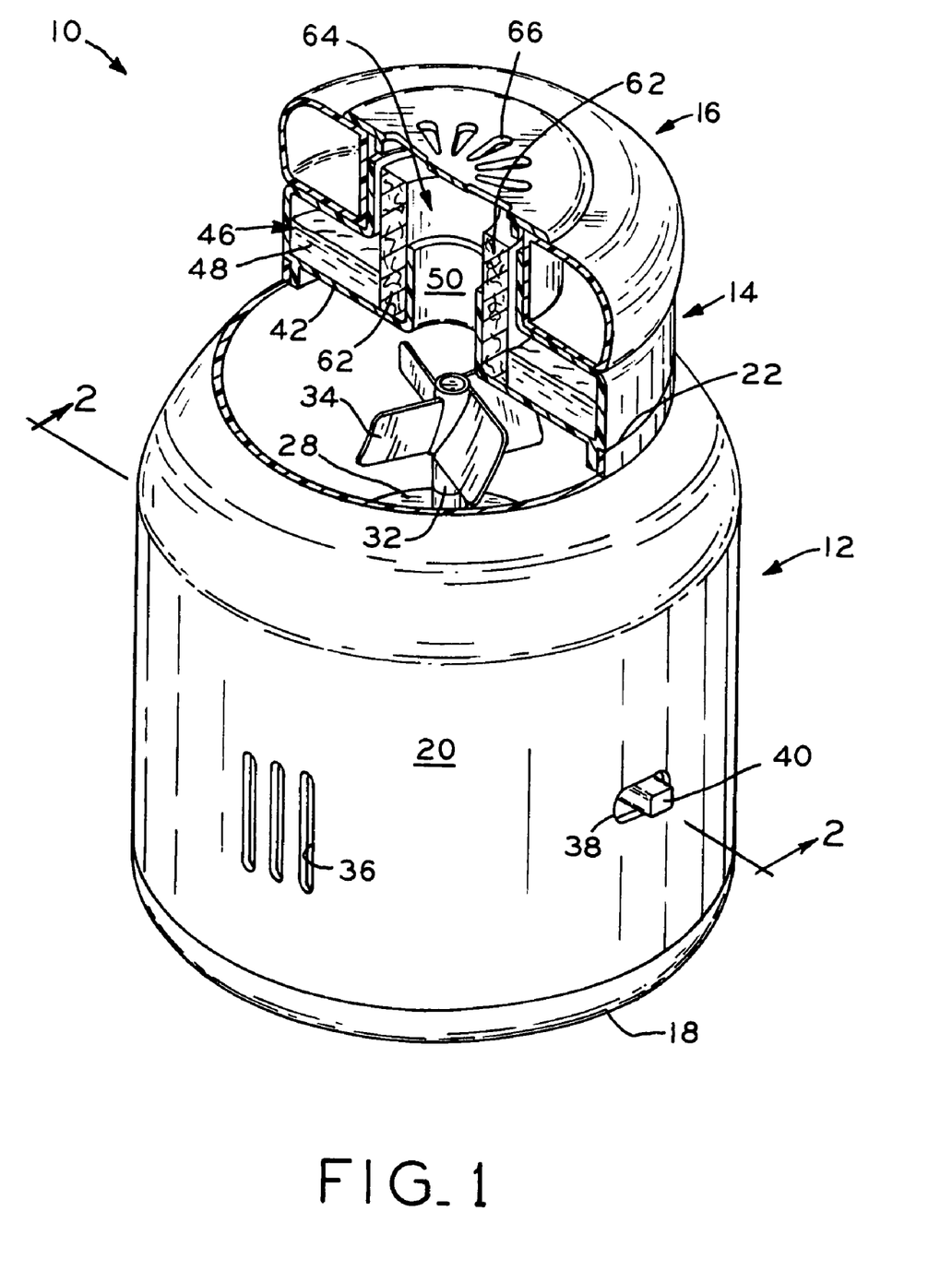
FIG. 1 is a partially sectioned, perspective view of a distribution device according to a first embodiment of the present disclosure.
Figure 2:
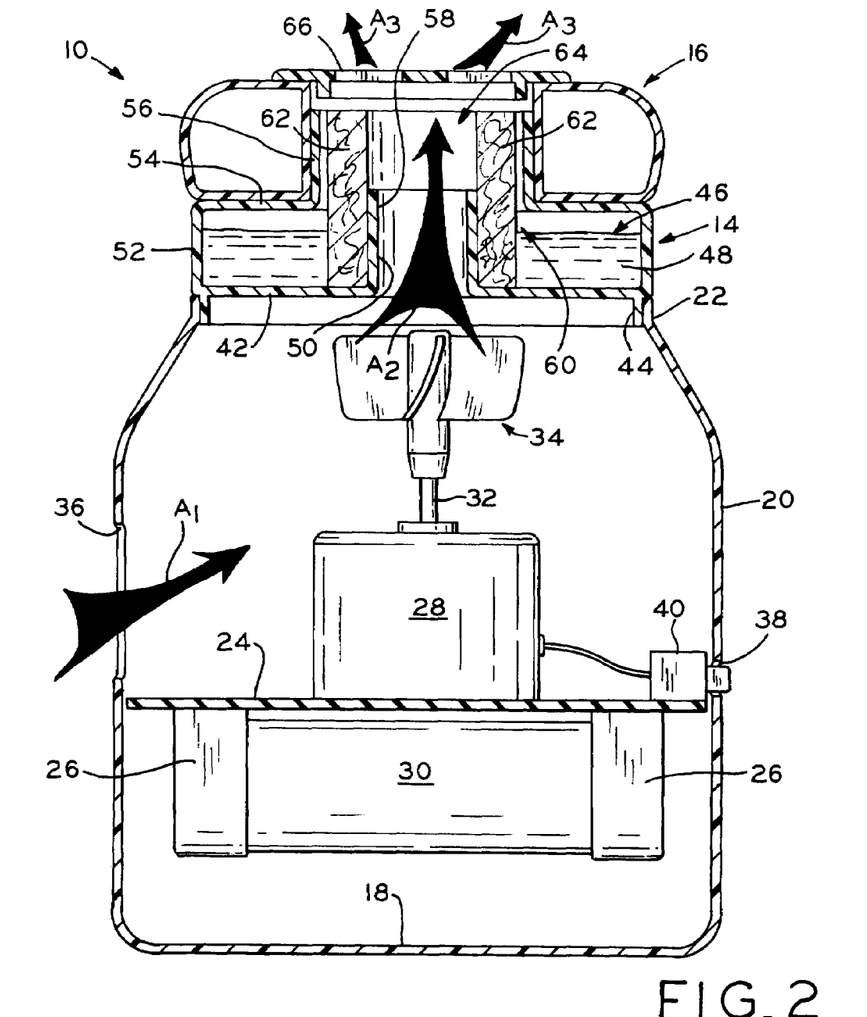
FIG. 2 is a sectional view of the device of FIG. 1, taken along line 2-2 of FIG. 1.
Figure 3:
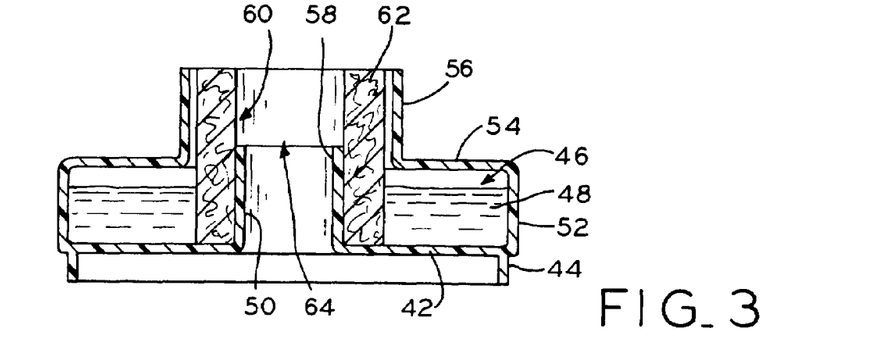
FIG. 3 is a sectional view of the liquid reservoir of the device of FIG. 1.

Referring to FIGS. 1-3, a device 10 for distributing a volatile fluid in air is shown according to one embodiment of the present disclosure. Device 10 may be an air freshener, an air cleaner, a pest control device, or other device, wherein the volatile fluid may be a scented liquid having a fragrance, a fungicide, an anti-allergenic substance, another type of disinfectant, or an insect repellant or insecticide, for example. As described in detail below, the distribution devices disclosed herein include an improved wick structure as well as a distribution mechanism for enhancing evaporation of the liquid and distribution of the liquid into the surrounding environment.

Distribution device 10 generally includes main housing 12, liquid reservoir 14 attached to an upper end of main housing 12, and cap 16 attached to an upper end of reservoir 14. Each of main housing 12, reservoir 14, and cap 16 may be made of a suitable rigid plastic or of metal, for example. Main housing 12 generally includes bottom wall 18 and a cylindrical side wall 20 defining an open upper end 22 to which reservoir 14 is attached via an adhesive, a press-fit, or by welding, for example.

Main housing 12 includes an internal wall 24 to which battery housing 26 and electric motor 28 are mounted. Battery housing 26 contains one or more batteries 30, as well as electrical contacts for conducting electrical current from batteries 30 to electric motor 28. Electric motor 28 may be a small DC motor, for example, and includes an output shaft or armature 32 to which an axial flow fan 34 is coupled. Side wall 20 of housing 12 includes one or more openings therein, shown herein as a plurality of slots 36, for allowing air to enter housing 12. Housing 12 additionally includes opening 38 through which switch 40 extends, which is electrically connected to motor 28 and batteries 30, and which may be actuated to close and open the electrical connection between batteries 30 and motor 28 to turn motor 28 on and off, respectively. Switch 40 may also include an intermediate position or positions for operating motor 28 at different speeds. Although motor 28 is disclosed herein as being powered by batteries 30, motor 28 may also be powered from an AC building outlet (not shown) via a direct plug-in connection between device 10 and the outlet or via a power cord extending between device 10 and the outlet. As discussed below, motor 28 and fan 34 comprise one type of distribution mechanism for enhancing the evaporation and distribution of the liquid contained within reservoir 14 into the surrounding environment.

Liquid reservoir 14 is shown in detail in FIG. 3, and generally includes bottom wall 42 with annular flange 44 fitted within open upper end 22 of main housing 12, and an annular shaped reservoir portion 46 containing a volatile liquid 48. Reservoir portion 46 is defined between bottom wall 42, internal boss 50, side wall 52, top wall 54, and external boss 56. External boss 56 defines an open upper end or outlet 58 of liquid reservoir 14. Internal boss 50 and external boss 56 together define a substantially annular space 60 therebetween in which wick 62 is disposed in liquid communication with reservoir portion 46 of reservoir 14.

Wick 62 has a substantially hollow structure, with a cylindrical or tubular profile defining a central passage 64 therethrough, and is received within annular space 60 about internal boss 50 of reservoir 14. Wick 62 may have other shapes, such as a square, polygonal, or other cross sections, and may include one or more hollow passages therethrough. Wick 62 may be formed of a porous ceramic, a porous paper material, or a porous plastic material such as polypropylene, for example. Some of these materials, particularly ceramic materials, may be sintered to provide a large number of pores therein. Advantageously, central passage 64 of wick 62 provides an increased exposed surface area of wick 62 as compared with known wicks having a solid cross section to thereby enhance evaporation and distribution of volatile liquid 48 within reservoir portion 46 of reservoir 14 from wick 62 into the surrounding environment.

Cap 16 is fitted about external boss 56 of liquid resrvoir 14 via a screw fit or a press-fit, for example, and includes a plurality of openings 66 therein which are disposed directly above wick 62 and central passage 64 of wick 62. In order to fill a volatile liquid within reservoir portion 46 of reservoir 14, cap 16 and wick 62 are removed, and the liquid is poured downwardly through annular space 60 into reservoir portion 46, followed by replacing wick 62 and cap 16. Alternatively, reservoir 14 may include a filler neck with a removable fill cap (not shown).

In use of device 10, volatile liquid 48 is carried upwardly from reservoir portion 46 through wick 62 via capillary action and is distributed to the surrounding environment via evaporation. In order to enhance the distribution of volatile liquid 48 into the surrounding environment, the distribution mechanism of device 10 is actuated, wherein switch 40 is moved to the "on" position to supply electrical current from batteries 30 to motor 28 to rotatably drive fan 34, thereby drawing air from the surrounding environment into main housing 12 through slots 36 as represented in FIG. 2 by arrow $A_1$. Thereafter, the air is forced upwardly through central passage 64 of wick 62 as represented by arrow $A_2$ in FIG. 2, wherein the air flow contacts wick 62 to enhance the evaporation of the liquid 48 within wick 62 into the air flow. The air flow, including the evaporated liquid, is then forced outwardly of device 10 through openings 66 in cap 16, as represented by arrows $A_3$ in FIG. 2, to distribute the evaporated liquid outwardly of device 10 into the surrounding environment.

Figure 4:
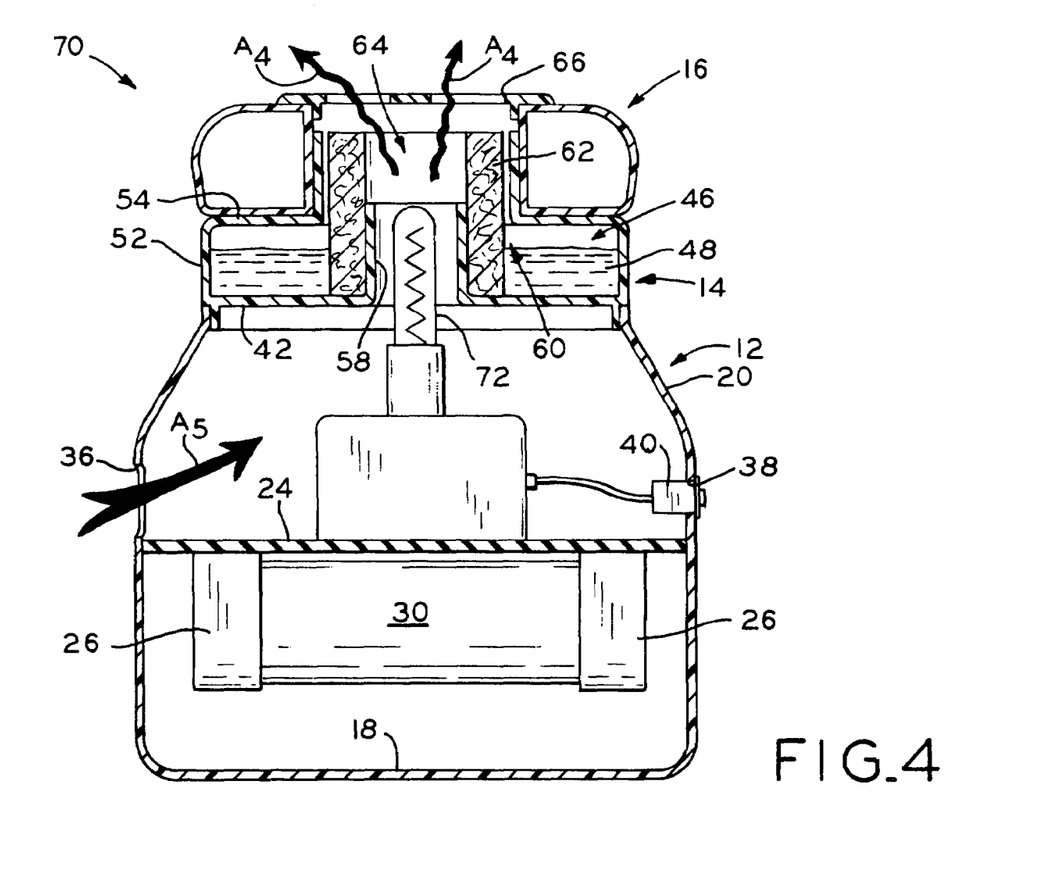
FIG. 4 is a sectional view of a distribution device in accordance with another embodiment of the present disclosure.

Referring to FIG. 4, another device 70 for distributing a volatile liquid in air is shown according to another embodiment of the present disclosure which, except as described below, is substantially identical to device 10 described above, and identical reference numerals will be used in FIG. 4 to identify identical or substantially identical features therebetween. Liquid distribution device 70 includes a distribution mechanism including heating element 72 in electrical contact with batteries 30 via switch 40. Heating element 72 may be a ceramic resistance heating element, for example, and may extend at least partially into central passage 64 of wick 62 such that heating element 72 is disposed closely proximate wick 62. Alternatively, heating element 72 may be disposed in its entirety within central passage 64 of wick 62, or may be disposed in its entirety externally of central passage 64 of wick 62. In an alternate embodiment, heating element 72 may be powered from an AC building outlet (not shown) via a direct plug-in connection between device 70 and the outlet or via a power cord extending between device 70 and the outlet.

In another alternative embodiment, heating element 72 may be formed as a candle with a flame extending toward central passage 64.

As illustrated in FIG. 4, when switch 40 is moved to an "on" position, electrical current from batteries 30 causes heating element 72 to heat via electrical resistance, for example, thereby in turn heating central passage 64 of wick 62 and wick 62 itself to cause volatilization or evaporation of the liquid 48 within wick 62. The heating of central passage 64 of wick 62 sets up a convection air flow within distribution device 70, wherein air heated in central passage 64 of wick 62 flows upwardly and exits device 70 through openings 66 in cap 16 along arrow $A_4$ in FIG. 4, thereby in turn drawing air into main housing 12 of device 70 through slots 36 toward central passage 64 of wick 62 along arrow $A_5$ of FIG. 4.

Figures 5, 5A, 5B, 6:
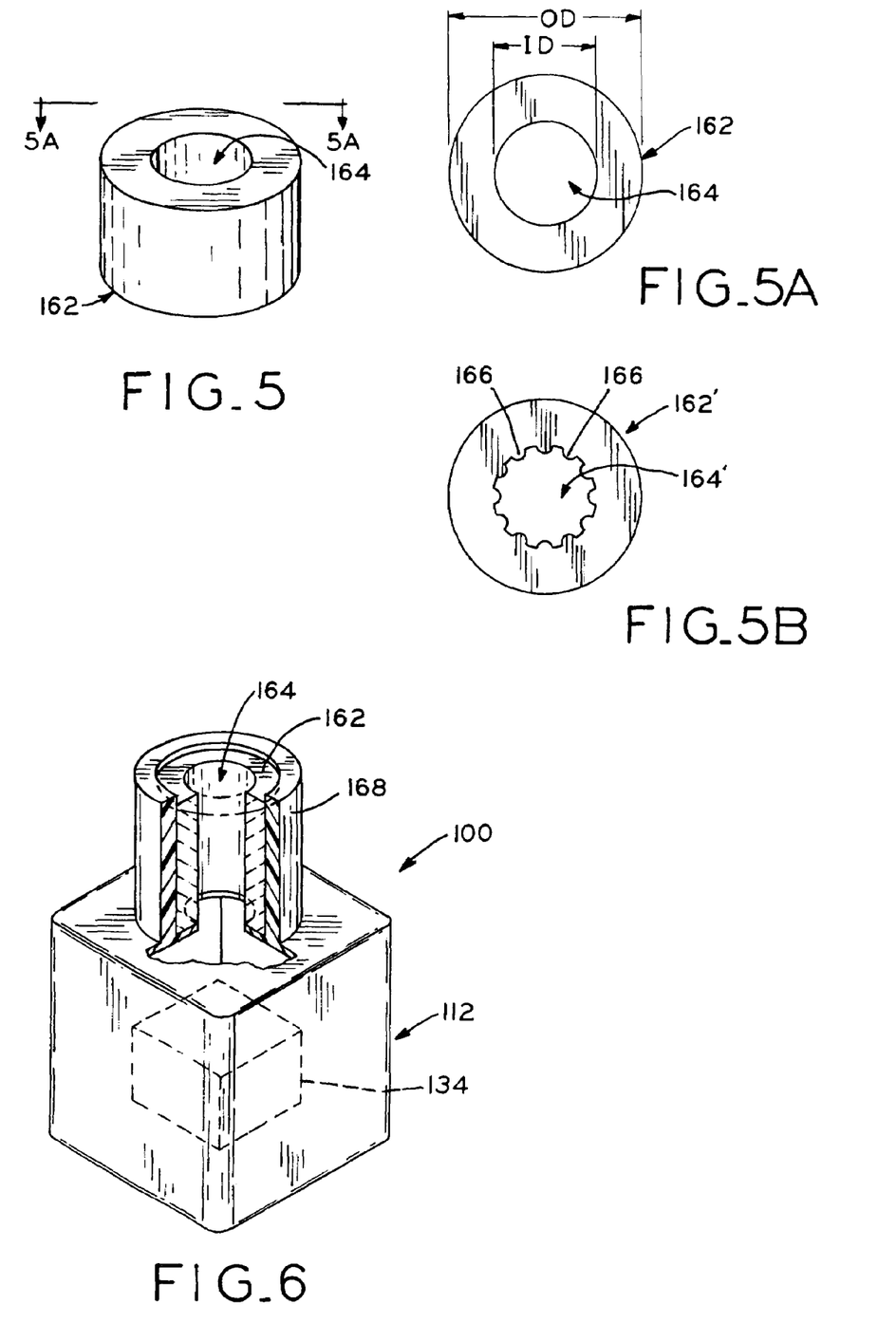
FIG. 5 is a perspective view of a wick for a distribution device in accordance with another embodiment of the present disclosure.
FIG. 5A is an end view of the wick of FIG. 5, taken along line 5A-5A of FIG. 5.
FIG. 5B is an end view of an alternative wick for a distribution device.
FIG. 6 is a partially sectioned, perspective view of a distribution device according to another embodiment of the present disclosure.

Referring now to FIG. 5, an alternative embodiment wick is illustrated. Wick 162 is solid, and may be shaped as a tubular structure defining a substantially hollow central passage 164. Wick 162 may be impregnated with a volatile fluid and may be used with devices 10 or 70, described above, or in the devices of FIGS. 6-9 described below, such that the liquid reservoir 14 of device 10 or 70 would be unnecessary. The volatile fluid, such as a scented liquid having a fragrance, a fungicide, an anti-allergenic substance, another type of disinfectant, or an insect repellant or insecticide, for example, could be contained within a highly porous structure, or may be captured within a carrier matrix which is molded into the shape of wick 162. In this embodiment, the wick 162, or a cartridge device containing wick 162, for example, may be mounted within a suitable receptacle within device 10 or 70, described above, or in the devices in FIGS. 6-9 described below.

As shown in FIG. 5A, wick 162 may have a generally tubular structure which has a generally circular cross-sectional shape. Wick 162 may define outer diameter OD and inner diameter ID. Outer diameter OD may be as small as 7/8", 1", 1 1/8", 1 1/4", 1 3/8", or 1 1/2" or as large as approximately 2", 1 7/8", 1 3/4" or 1 5/8", for example. Inner diameter ID may be as small as 1/8", 1/4", 3/8", or 1/2" or as large as approximately 1", 7/8", 3/4", or 5/8", for example. As shown in FIG. 5B, an alternative wick 162', which is substantially similar to wick 162 (FIGS. 5 and 5A), may include a plurality of projections 166 which project into central passage 164' to increase the surface area between the interior of wick 162' and the air flow moving therethrough. In alternative embodiments, wick 162 may have a cross-sectional shape in the form of an ellipse, a polygon, or a non-regular shape.

In an exemplary embodiment, wick 162 may be formed of a polymer material and a volatile fluid impregnated within the polymer material. The volatile fluid may form as little as 10%, 15%, 20%, 25%, 30%, 35%, 40%, or 45% of the total weight of wick 162 or may form as much as 95%, 90%, 85%, 80%, 75%, 70%, 65%, 60%, 55%, or 50% of the total weight of wick 162, for example with the remainder formed of the polymer material. In one embodiment, the greater the percentage of the total weight of wick 162 which is formed by the volatile fluid, the larger the effective life of wick 162. The volatile fluid may be, for example, a liquid fragrance commercially available as 190196K Sunshine Fruits fragrance from Firmenich Company of Geneva, Switzerland. The polymer material may be formed as a plastic commercially available as Pebax 2533SN01 Polyether Block Amide from Arkema Inc. of Philadelphia, Pa. Wick 162 may be formed as a solid material which has a degree of flexibility. In an exemplary embodiment, wick 162 is a solid, non-porous structure, i.e., wick 162 contains no open cell structures or pores on a macroscopic level and is substantially impermeable to water and air.

In operation, wick 162 may formed by heating and mixing the polymer material and the volatile fluid to approximately 300° F. The mixture is then cooled to a gel or solid viscous form which can be formed into a desired shape, such as a tube. Forming the desired shape can be effected via a number of manufacturing methods, such as by compression molding, for example.

In one embodiment, the desired shape is formed via a potting or casting method in which the mixture is combined in a heated container and is then poured into a mold of the desired shape after which the mixture is allowed to cool.

In another embodiment, the mixture of the polymer material and the volatile fluid is mixed in an extrusion machine under appropriate heat and pressure. The mixture is then pushed through an extrusion die to form the desired shape, which is then allowed to cool and cut into individual wicks 162. This method may be a continuous process.

In yet another embodiment, the mixture of the polymer material and the volatile fluid is mixed in an injection molding machine under appropriate heat and pressure. The mixture is then injected into a mold where the mixture is cooled to form the desired shape. This method may be an incremental process.

Wick 162, which includes the polymer material and the volatile fluid, may slowly dispense the volatile fluid into the air over a period of time via evaporation and volatilization. For example, wick 162 may release the volatile fluid in an average amount of 100 milligrams per day for approximately 30 to 60 days. The release rate may decrease over time and may depend upon the configuration of the polymer material and the volatile fluid. The tubular shape of wick 162 provides an advantage for volatile fluid release and appliance design.

Increasing the air flow through central passage 164 of wick 162 may improve the release performance of the volatile fluid by increasing the amount of volatile fluid which is released via evaporation and volatilization. As shown in FIG. 6, air flow through central passage 164 may be controlled or effected via a distribution mechanism or activation element 134, which may be fan 34 or heating element 72 described above with reference to the embodiments of FIG. 2 and FIG. 4, respectively, to aid in evaporation and distribution of the volatile fluid from wick 162. Fan 34 and/or heating element 72 may be turned on and off periodically to control release rates of the volatile fluid. Wick 162 may include cap structures (not shown) at either end thereof to limit air flow through central passage 164 to provide greater control of release of the evaporated volatile fluid. The cap structures may include ventilation apertures which may be selectively opened or closed to vary the air flow through central passage 164. Alternatively, wick 162 may be mounted for rotation by an air flow through central passage 164 enhance release of the evaporated volatile fluid. For example, wick 162 may include internal or external surfaces having inclined blades and/or a continuous helical surface such that airflow proximate the internal and/or external surfaces generates rotation of wick 162. In one embodiment, compressed air may be pushed through central passage 164 at periodic intervals to control release of the evaporated volatile fluid. In another embodiment, wick 162 may be positioned proximate to other air flow devices, such as home or automotive heating/cooling vents, for example, to improve air flow through central passage 164.

Figure 9:
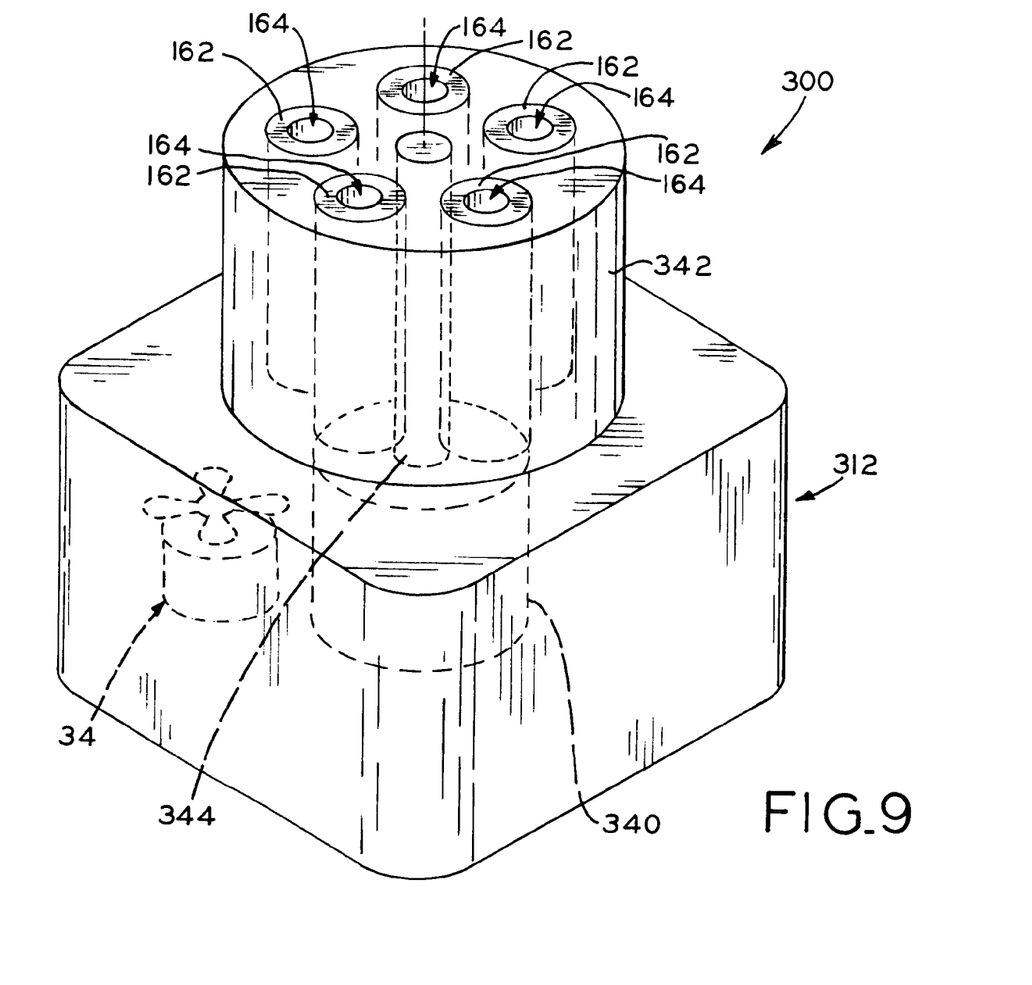
FIG. 9 is a perspective view of a distribution device according to another embodiment of the present disclosure.

After a designated period of use, i.e., when most or all of the volatile fluid originally impregnated within wick 162 has been volatized therefrom, wick 162, or a cartridge device containing wick 162, would be replaced with a new wick 162 or cartridge device. Thus, wick 162 may be disposable and replaceable. In one embodiment, the device for distributing the volatile liquid in air which includes wick 162 may include a plurality of wicks 162 of which one wick 162 may be loaded into position for use and, after a designated period of use, rotated out of position and a new wick 162 is positioned for use. As shown in FIG. 9, device 300 may include housing 312, which may be substantially identical to housing 12 (FIG. 2), described above, fan 34, motor 340, wick housing 342, and a plurality of wicks 162. Wick housing 342 may accept a plurality of wicks 162 therein and fan 34 may be used to aid in evaporation of the volatile fluid from each wick 162. Upon exhaustion of the volatile fluid in a particular wick 162, motor 340 rotates housing 312 via rotation of shaft 344 until a fresh wick 162 is positioned proximate fan 34. Advantageously, this embodiment reduces the amount of times a user must change wick 162 or the plurality of wicks 162 in the device. In this embodiment, each wick 162 may vary in the composition of the volatile fluid, such as having two differently scented liquid fragrances, for example.

Wick 162 may be used in distribution devices which are equipped for various applications, some of which are described in further detail above, such as an AC version for use with home outlets, a DC version for use with mobile applications which integrate batteries, a DC version for use with car outlets, and a non-powered version which may be used proximate home or automotive heating/cooling vents.

Referring again to FIG. 6, a device 100 for distributing volatile fluids in air may include wick 162 and housing 112. Housing 112 may include distribution or activation element 34, 72, as described above. Wick 162 is positioned proximate element 34, 72 such that air flow is effected through central passage 164 of wick 162. Outside shell 168 may be included to surround wick 162 and protect wick 162 during handling thereof. Shell 168 may prevent a handler from coming into direct physical contact with the volatile fluid impregnated in wick 162. Moreover, shell 168 reduces evaporation of the volatile fluid from the exterior surface of wick 162. In one embodiment, shell 168 may be formed of a suitable rigid plastic, for example, such as polypropylene.

Figure 7:
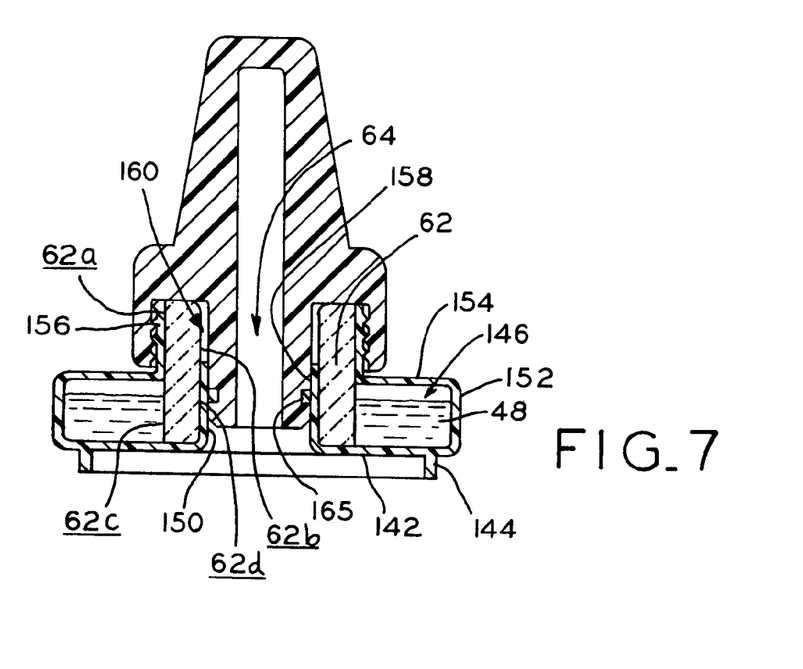
FIG. 7 is a sectional view of a distribution device according to another embodiment of the present disclosure.

Referring to FIG. 7, an alternative embodiment liquid reservoir 114 is shown which, except as described below, is substantially identical to liquid reservoir 14 described above with respect to FIG. 3, and identical reference numerals will be used in FIG. 7 to identify identical or substantially identical features therebetween. Liquid reservoir 114 may include bottom wall 142 with annular flange 144 which may be fitted within open upper end 22 (FIG. 2) of main housing 12 (FIG. 2), and an annular shaped reservoir portion 146 containing a volatile liquid 48. Reservoir portion 146 is defined between bottom wall 142, internal boss 150, side wall 152, top wall 154, and external boss 156. External boss 156 defines an open upper end or outlet 158 of liquid reservoir 114. Internal boss 150 and external boss 156 together define a substantially annular space 160 therebetween in which wick 62 is disposed in liquid communication with reservoir portion 146 of reservoir 114.

Wick 62 defines central passage 64 therethrough, and is received within annular space 160 about internal boss 150 and within external boss 156 of reservoir 114. Lower inner surface 62d of wick 62 abuts and forms a close fitting engagement with internal boss 150. Upper outer surface 62a abuts and forms a close fitting engagement with external boss 156. Upper inner surface 62b is in communication with the surrounding environment when in use. Lower outer surface 62c is in fluid communication with volatile liquid 48. The close fitting and abutting relationship between wick 62 and reservoir 114 advantageously prevents or retards spillage of volatile liquid 48 in the event that the device is tipped, for example, and simultaneously advantageously eliminates evaporation of volatile liquid 48 directly from reservoir portion 146 into the surrounding environment. Moreover, lower outer surface 62c of wick 62 is advantageously in fluid communication with volatile liquid 48 such that liquid 48 may advance toward the upper portion of wick 62 via capillary action to reach upper inner surface 62b, and, upon air flow through central passage 64, the volatile liquid 48 is evaporated into the surrounding air.

Cap 116 may be selectively placed about external boss 156 of liquid reservoir 114 via a screw fit arrangement, or a press-fit engagement (not shown), for example. O-ring 165 may be provided to effectively seal liquid reservoir 114 and cap 116 to prevent any accidental spillage of volatile liquid 48 and/or undesired evaporation of volatile liquid 48 prior to removal of cap 116. In order to fill a volatile fluid within reservoir portion 146 of reservoir 114, cap 116 and wick 62 are removed, and the fluid is poured downwardly through annular space 160 into reservoir portion 146, followed by replacing wick 162 into annular space 160 and optionally attaching cap 116. In another embodiment, reservoir 114 may include a filler neck with a removable fill cap (not shown) to facilitate filling reservoir portion 146 with volatile liquid 48.

Figure 8:
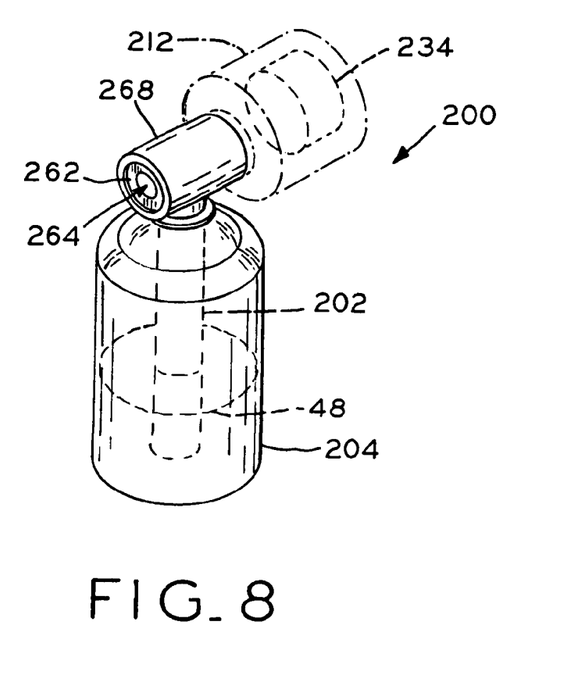
FIG. 8 is a perspective view of a distribution device according to a further embodiment of the present disclosure.

Referring now to FIG. 8, a device 200 for distributing a volatile fluid in air is shown according to another embodiment of the present disclosure. Device 200 may include shaft 202 extending into reservoir 204 containing a volatile liquid 48. Shaft 202 may be formed of substantially the same material used to form either wick 62 (FIGS. 1-4 and 7) or wick 162 (FIGS. 5, 5A, 5B, and 6) such that volatile liquid 48 advances toward the top of reservoir 204 via capillary action. For example, shaft 202 may be formed of a polypropylene material, a rope-type material, or any other porous wicking material. Volatile liquid 48 is advanced upwards via capillary action until it reaches wick 262 disposed in shell 268. Shell 268 may be substantially identical to shell 168 (FIG. 6), described above. Wick 262 may be substantially identical to wick 62 (FIGS. 1-4 and 7) and/or 162 (FIGS. 5, 5A, 5B, and 6), described above, such that movement of air through central passage 264 via distribution or activation element 234, which may be fan 34 or heating element 72 described above with reference to the embodiments of FIG. 2 and FIG. 4, respectively, housed in housing 212, which is substantially identical to housing 12 (FIG. 2), described above, effects evaporation of volatile liquid 48 into the surrounding air.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A device for distributing a fluid into a surrounding environment, comprising:
 a housing;
 a wick defining a passage extending therethrough from one end of said wick to another, opposite end of said wick, said wick including a fluid, said wick in airflow communication with said housing and in airflow communication with the surrounding environment; and an activating element positioned within said housing for effecting a flow of air through said passage from said one end of said wick to said other end of said wick and distributing said fluid into the surrounding environment.

2. The device of claim 1, wherein said wick comprises a polymer material and said fluid, said polymer material and said fluid co-formed with one another wherein said fluid is captured within, and distributed throughout, said polymer material.

3. The device of claim 2, wherein said fluid comprises between approximately 80% and 90% by weight of said wick.

4. The device of claim 1, further comprising a shell at least partially surrounding said wick and associated with said housing.

5. The device of claim 1, wherein said activating element comprises a fan, said fan driven by a power source and providing the flow of air through said passage of said wick.

6. The device of claim 1, wherein said activating element comprises a heating element in connection with a power source, said heating element disposed proximate said passage of said wick.

7. A device for distributing a fluid into a surrounding environment, comprising:
   a housing;
   a solid wick defining a passage therethrough, said wick impregnated with a fluid, said wick in airflow communication with said housing and the surrounding environment; and
   an activating element positioned within said housing for effecting distribution of said fluid into the surrounding environment, said activating element including a heating element in connection with a power source, wherein said heating element is at least partially disposed within said passage of said wick.

8. The device of claim 1, wherein said fluid comprises a volatile liquid.

9. The device of claim 8, wherein said volatile liquid is selected from the group consisting of a scented liquid, a fungicide, a disinfectant, an anti-allergenic substance, an insect repellant, and an insecticide.

10. The device of claim 1, wherein said passage defines an inner surface of said wick, said inner surface including a plurality of surface discontinuities.

11. A device for distributing a fluid into a surrounding environment, comprising:
   a housing including a reservoir containing a fluid;
   said reservoir including an inner wall and an outer wall defining an opening;
   a substantially hollow wick defining a passage therethrough, said wick in fluid communication with the surrounding environment and the housing, said wick disposed between said inner wall and said outer wall, said wick abutting both said inner wall and said outer wall; and
   an activating element disposed at least partially within said housing for effecting distribution of said fluid into the surrounding environment.

12. The device of claim 11, wherein said wick includes an upper inner surface and a lower outer surface, said upper inner surface in fluid communication with the surrounding environment and said lower outer surface in fluid communication with said fluid.

13. The device of claim 11, wherein said wick includes an upper outer surface and a lower inner surface, said upper outer surface of said wick in abutting engagement with said outer wall of said reservoir and said lower inner surface of said wick in abutting engagement with said inner wall of said reservoir.

14. The device of claim 11, further comprising a cap, said cap selectively attached to said reservoir.

15. The device of claim 11, wherein said wick has a substantially tubular shape defining said passage.

16. The device of claim 11, wherein said activating element comprises a fan, said fan driven by a power source and providing a flow of air through said passage of said wick.

17. The device of claim 11, wherein said activating element comprises a heating element in connection with a power source, said heating element disposed proximate said passage of said wick.

18. The device of claim 17, wherein said heating element is at least partially disposed within said passage of said wick.

19. The device of claim 11, wherein said fluid comprises a volatile liquid.

20. The device of claim 19, wherein said volatile liquid is selected from the group consisting of a scented liquid, a fungicide, a disinfectant, an anti-allergenic substance, an insect repellant, and an insecticide.

21. A device for distributing a fluid into a surrounding environment, comprising:
   a housing;
   a solid wick comprising a polymer material and a fluid, said polymer material and said fluid co-formed with one another wherein said fluid is captured within, and distributed throughout, said polymer material, said wick defining a passage therethrough, said passage in airflow communication with said housing and with the surrounding environment; and
   an air flow activating element positioned within said housing, said element effecting a flow of air through said passage of said wick and distributing said fluid into the surrounding environment.

22. The device of claim 21, wherein said passage defines an inner surface of said wick, said inner surface including a plurality of surface discontinuities.

23. The device of claim 21, wherein said wick defines a longitudinal axis, said passage extending along said longitudinal axis.

* * * * *